United States Patent [19]

Hurscham

[11] 3,946,732

[45] Mar. 30, 1976

[54] TWO-CHAMBER MIXING SYRINGE

[75] Inventor: Alfred A. Hurscham, Hudson, Ohio

[73] Assignee: Ampoules, Inc., Macedonia, Ohio

[22] Filed: July 18, 1974

[21] Appl. No.: 489,746

Related U.S. Application Data

[63] Continuation-in-part of Ser. No. 386,594, Aug. 8, 1973, abandoned.

[52] U.S. Cl.... 128/218 M; 128/218 F; 128/218 DA
[51] Int. Cl.²......................................... A61M 5/00
[58] Field of Search.... 128/218 M, 218 D, 218 DA, 128/218 PA, 218 C, 220, 234, 272, 215, 216, DIG. 28, 235, 237

[56] References Cited

UNITED STATES PATENTS

| | | | |
|---|---|---|---|
| 2,159,217 | 5/1939 | Lozier et al. | 128/218 M |
| 2,193,322 | 3/1940 | Lozier et al. | 128/218 M |
| 2,567,001 | 9/1951 | Watson | 128/218 M |
| 2,591,706 | 4/1952 | Lockhart | 128/218 M |
| 2,687,728 | 8/1954 | Copen | 128/218 D |
| 2,778,360 | 1/1957 | Miskel | 128/218 D |
| 3,380,451 | 4/1968 | Porter et al. | 128/218 M |
| 3,403,679 | 10/1968 | Sinclair et al. | 128/218 F |
| 3,438,373 | 4/1969 | Pannier, Jr. | 128/214.4 |
| 3,467,097 | 9/1969 | Ogle | 128/DIG. 28 |
| 3,469,572 | 9/1969 | Nehring | 128/2 F |

FOREIGN PATENTS OR APPLICATIONS

| | | | |
|---|---|---|---|
| 110,450 | 4/1964 | Czechoslovakia | 128/218 PA |

Primary Examiner—John D. Yasko
Attorney, Agent, or Firm—McNenny, Farrington, Pearne & Gordon

[57] ABSTRACT

Two-chamber syringes for mixing a powdered medicament with a diluent and then injecting the mixed ingredients into a patient are disclosed, together with a technique for assembling those syringes. According to one aspect of the invention, the syringe includes a vial formed with a single glass cylinder closed at one end by a plunger and at its other end by a pierceable diaphragm. An intermediate pierceable diaphragm divides the cylinder into upper and lower chambers, and is locked against axial movement relative to the cylinder. A powdered medicament is provided in the upper chamber and a diluent is provided in the lower chamber. The ingredients are mixed by inserting the vial into a cup-shaped holder having a hollow, pointed needle extending from the base of the holder. Axial pressure on the vial causes the pointed end of the needle to sequentially pierce the end intermediate diaphragms, and to cause the diluent to flow into an opening in the sidewall of the needle, through the needle, and then into the upper chamber from the pointed needle end. The thus-mixed ingredients are dispensed by applying axial pressure to the plunger, or by drawing metered amounts into the medicament pressurizing chamber of a needleless, hypojet injector.

25 Claims, 20 Drawing Figures

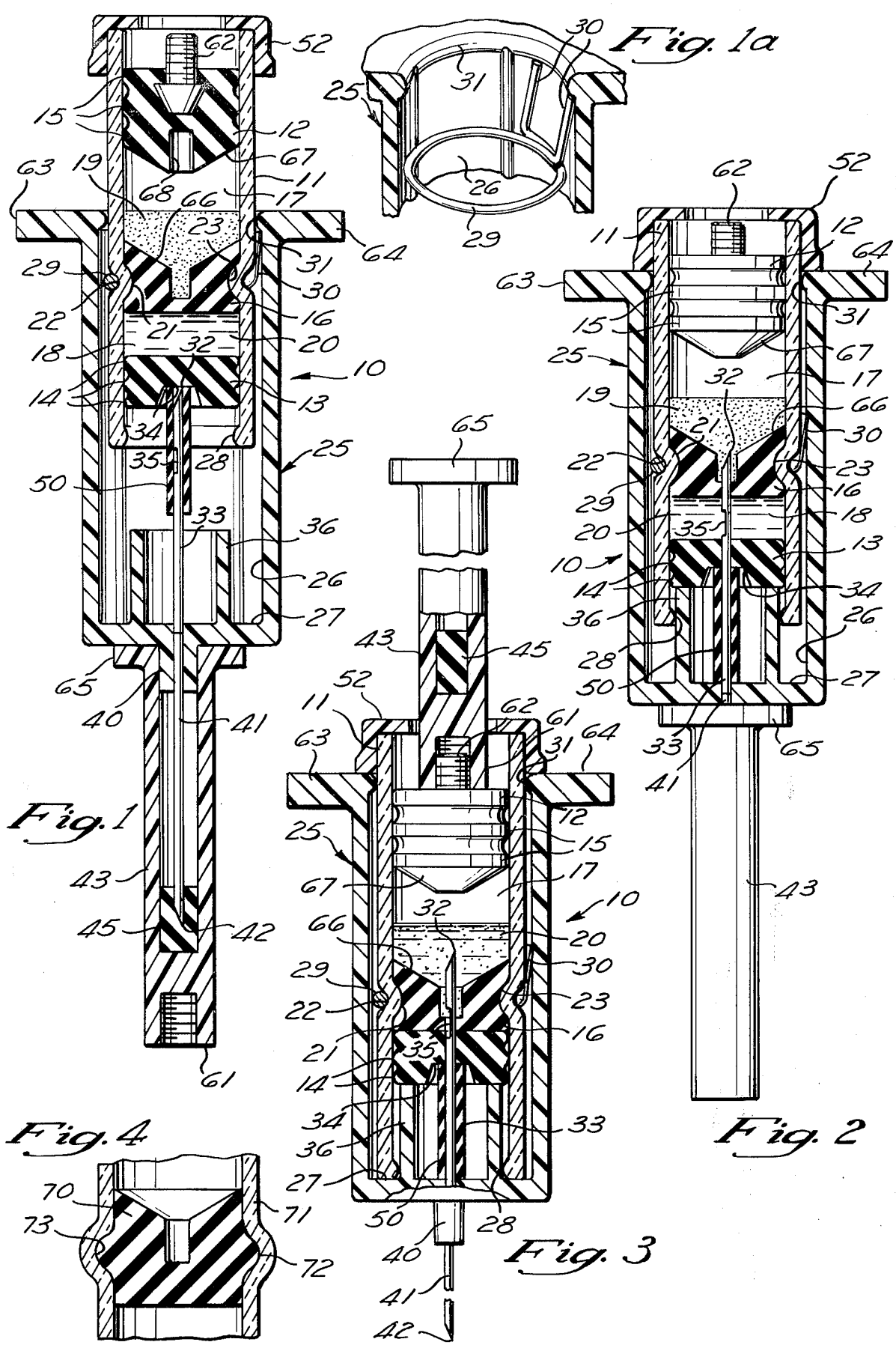

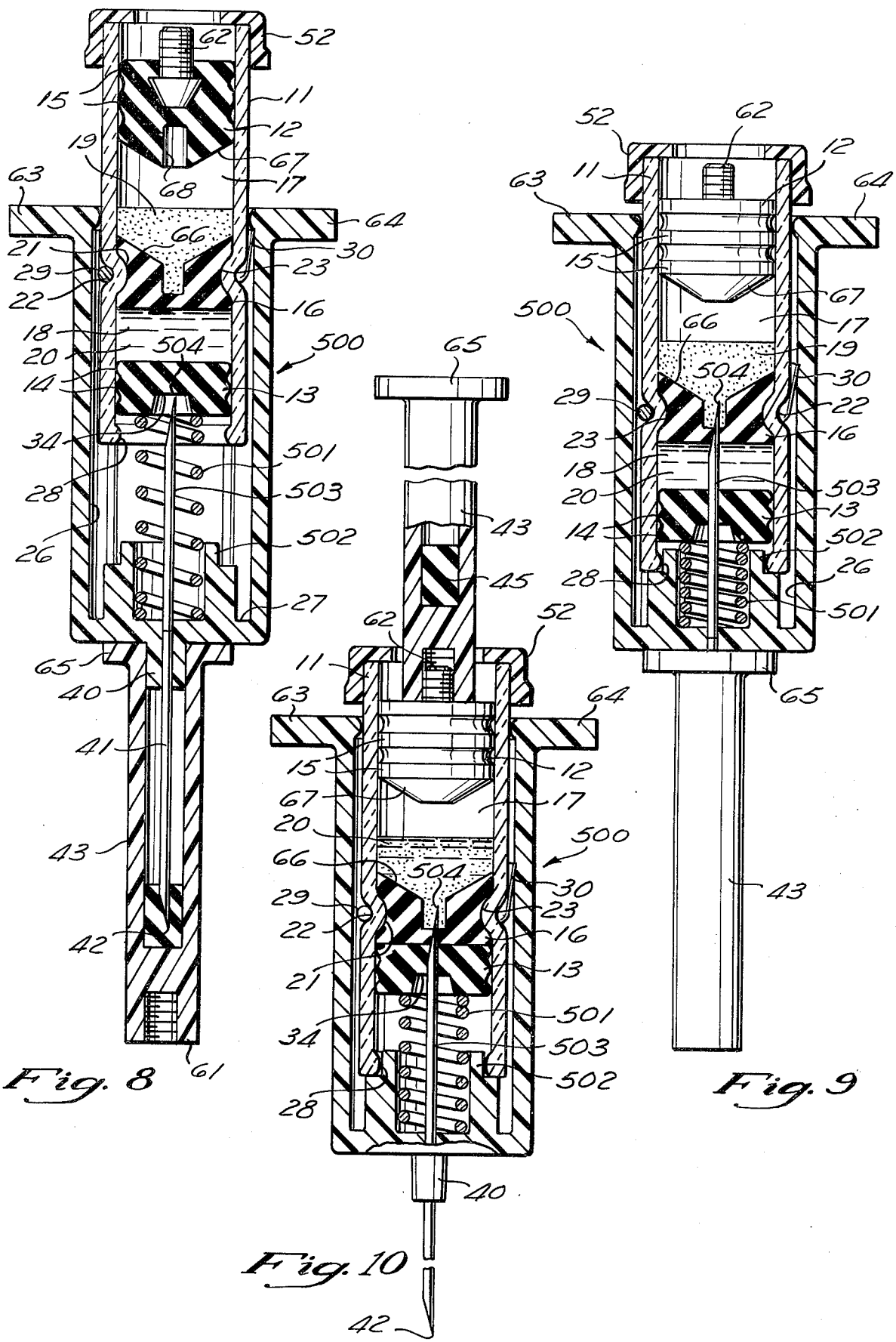

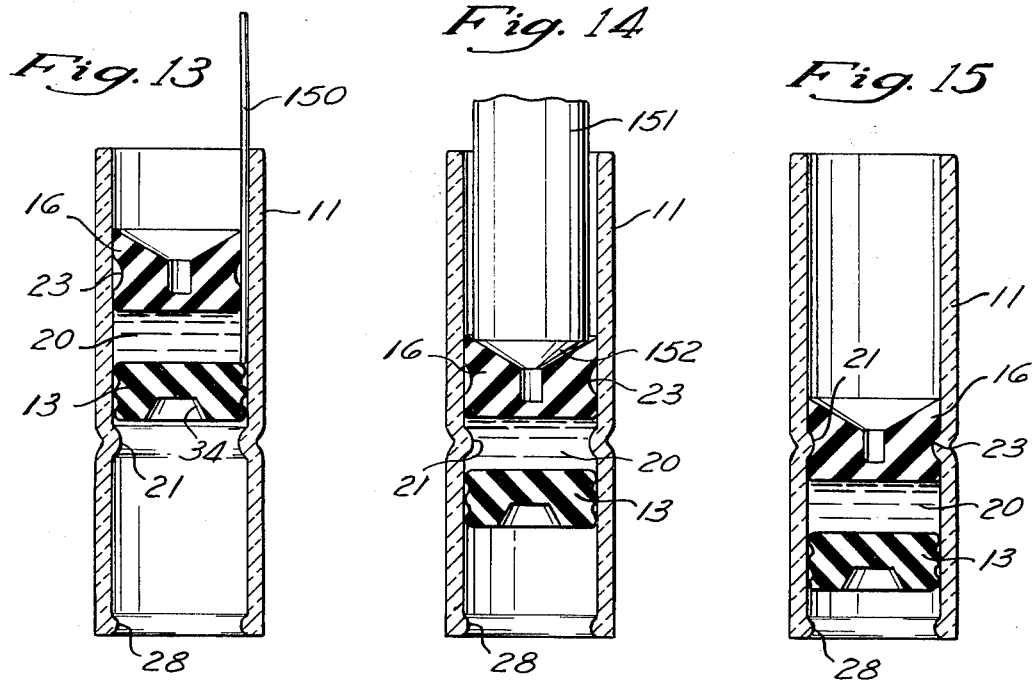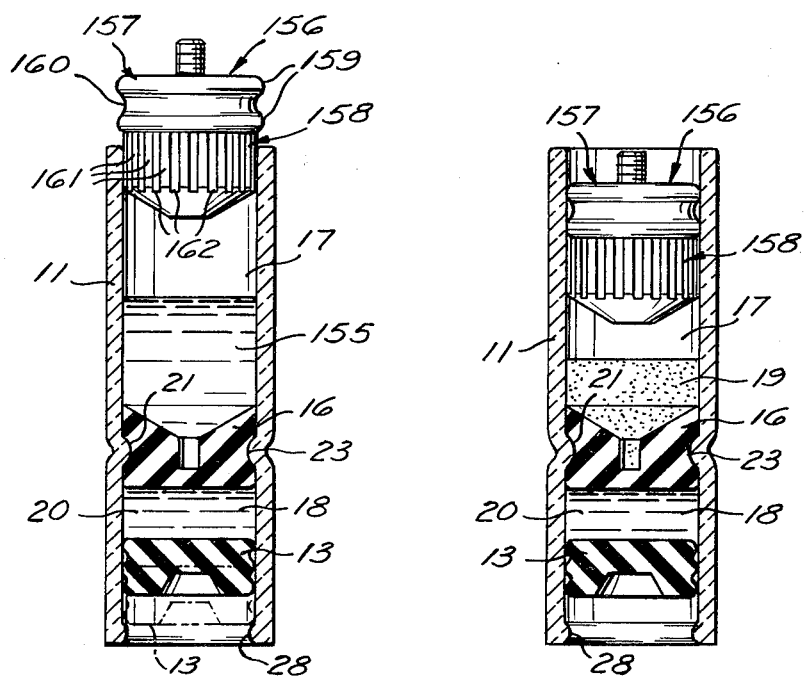

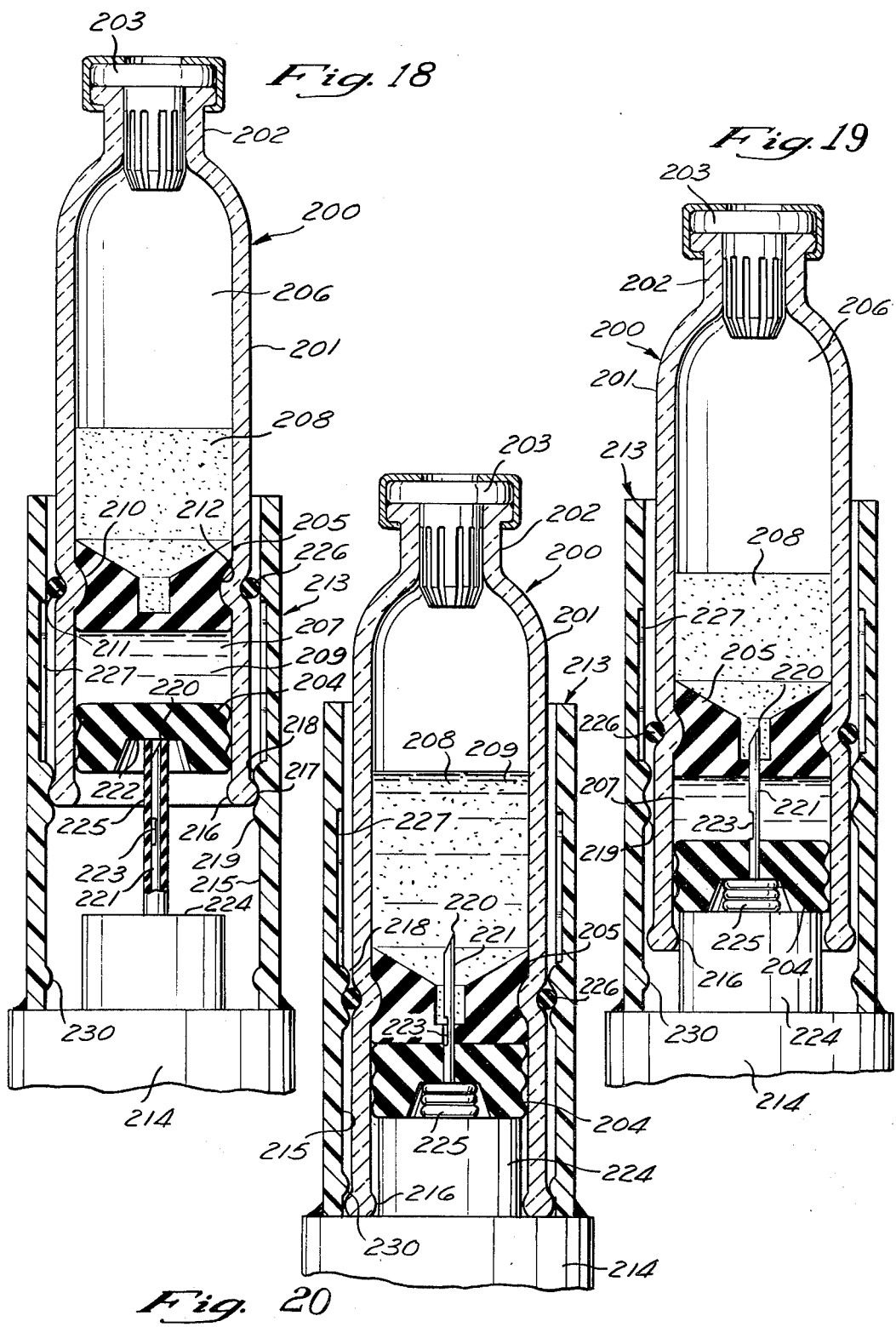

TWO-CHAMBER MIXING SYRINGE

RELATED APPLICATION

This application is a continuation-in-part of my co-pending application Ser. No. 386,594, filed Aug. 8, 1973 now abandoned.

BACKGROUND OF THE INVENTION

This invention relates to disposable hypodermic ampoules having two chambers for mixing a powdered medicament with a diluent prior to injecting the mixed ingredients into a patient through a needle externally affixed to the ampoule.

A number of drug compounds, including some antibiotics, some vaccines, and several other injectable products, require that an active ingredient (usually in a powder form) be mixed with an injection vehicle or diluent (usually water) shortly before administration. One widely accepted procedure for mixing powder and liquid medicament components is to provide them in separate vials, each having its own rubber stopper closing its outlet opening. The liquid is withdrawn from its vial by a needle and syringe, and is then injected into the vial containing the powder. The thus-mixed liquid and powder in the latter vial, after shaking it where required, is withdrawn as a dispersion by the same needle and syringe, and the injection is effected therewith in a conventional manner.

Since this is a relatively cumbersome and time-consuming technique, and since it requires careful handling of the syringe during the mixing operation to maintain sterility of the needle prior to the injection, attempts have been made to provide an injection syringe which itself contains the powder and liquid medicaments in separate chambers which are arranged so that the powder and liquid medicaments may be mixed just prior to an injection. Those ampoules may be broadly classified into contained-needle type injection devices and external needle-type injection devices.

The contained-needle type injection device is shown and described in U.S. Pat. No. 3,735,761 to Hurschman et al. In that patent, there is disclosed a multi-chamber, hypodermic device which includes first and second coaxially disposed cylinders. The cylinders respectively provide first and second medicament-containing chambers, the adjacent ends of which are separated by a first, puncturable, piston-like diaphragm. This first diaphragm extends across and around the end of the first cylinder to close and seal the same, and is slidably mounted in the adjacent end of the second cylinder to close and separately seal the same. The other end of the first cylinder slidably carries a plunger and a hypodermic needle is mounted on the plunger with its pointed end extending axially toward a pierceable, central portion of the first diaphragm. The other end of the second cylinder is closed and sealed by a puncturable diaphragm having its pierceable portion also axially aligned with the pointed end of the needle. A powder medicament in the first chamber and a liquid medicament in the second chamber are mixed by partially depressing the plunger so that the pointed end of the needle cannula pierces the first diaphragm. Liquid flows from the second chamber through the needle and into the first chamber as the first diaphragm moves toward and into engagement with the second diaphragm, thus mixing the two medicaments. An injection may be effected by further depressing the plunger to the end of its stroke while holding the ampoule against the skin of the patient.

While contained-needle type injection devices are suitable for many injection purposes, many physicians and nurses prefer to perform an injection with a more conventional syringe having an external needle which is manually inserted into the skin of the patient, since contained-needle type devices are primarily suited for use in a mechanical spring-actuated applicator. While the use of applicators has many advantages, it is impossible to express air from the ampoule prior to an injection and is impossible to aspirate the syringe during an injection to ensure that a blood vessel is not pierced by the needle. Also, applicators are not entirely suitable for veterinary use, since animals vary in size and coat.

In view of these problems, attempts have been made to provide two-chamber syringes having an external needle which are adapted to perform a standard injection after mixing the medicaments within the syringe. For example, U.S. Pat. No. 3,342,180 provides a vial which is separated into two chambers by a plunger. Powder is provided in a lower chamber and liquid is provided in the upper chamber. The plunger is provided with a one-way check valve so that upon retraction of the plunger, the liquid is forced through the valve and into the compartment containing the powder. The vial is provided with an external needle at its lower end so that the mixed medicament may be injected into the patient. This arrangement involves complicated valving in the separating plunger and therefore requires extremely complex plunger molding operations. A similar arrangement is shown in U.S. Pat. No. 3,330,280, wherein a plunger is provided with a displaceable plug to provide communication between the two chambers prior to injection. Other patents, such as U.S. Pat. No. 2,591,046, include complex passageways formed into the glass sidewall of the vial to provide communication between two chambers upon movement of an intermediate diaphragm. A major deficiency of prior art two-chamber devices is that, while they appear theoretically feasible, they are difficult, if not impossible, to assemble, fill, and/or freeze-dry with conventional equipment and know-how.

A more acceptable two-chamber syringe is set forth in U.S. Pat. No. 2,193,322. In that patent, the patentees provide a two-chamber injection device having an end diaphragm and an intermediate diaphragm which are sequentially pierced by one pointed end of a double-pointed needle to provide communication between the two chambers. Since the two chambers are illustrated as having fluid therein, the intermediate diaphragm is hydraulically locked against movement relative to the vial. Therefore, although the device according to that patent is suitable for mixing and then injecting two liquids, it is not suitable for mixing a liquid with a powder, since the intermediate diaphragm would not be hydraulically locked in position and would be moved by the piercing needle upon engagement. Furthermore, the device shown in that patent is not capable of having air expressed from the mixed medicament chamber prior to an injection, since air would be trapped between the opening at the end of the needle and the intermediate diaphragm upon plunger movement.

SUMMARY OF THE INVENTION

This invention provides a two-chamber mixing and injecting syringe having, or capable of being provided with, an external needle which overcomes these prior art problems. According to one aspect of the invention, the syringe includes a cylindrical, glass vial closed at one end by a plunger which is slidable relative to the vial and is closed at its other end by a pierceable diaphragm. An intermediate diaphragm divides the vial into first and second chambers, and that diaphragm is locked against axial movement relative to the vial. The lock is preferably a circumferential indentation in the sidewall of the vial to reduce the cross sectional area of the vial at that location. The intermediate diaphragm has a groove which is engaged by the indentation. A powdered medicament is provided in the chamber between the intermediate diaphragm and the plunger, and a diluent is provided in the other chamber. These ingredients are mixed by inserting the vial in a cup-shaped holder having a hollow, pointed needle extending through the base of the holder. Axial pressure on the vial causes the pointed end of the needle to sequentially pierce the end and intermediate diaphragms. The locking means ensures that the intermediate diaphragm will not be moved by the piercing needle. Diluent flows into an opening in the sidewall of the needle, through the needle, and then into the chamber containing the powdered medicament from the pointed needle end. The mixed ingredients are dispensed by applying axial pressure to the plunger.

Restraining intermediate diaphragm movement toward the end diaphragm is important in those situations where the powdered medicament is lyophilized in its chamber. Since the diluent is frozen and then thawed during the lyophilization cycle, an expansion takes place when the diluent is frozen and then a contraction of the chamber takes place upon thawing. If the intermediate diaphragm is not locked against movement toward the end diaphragm, the intermediate diaphragm and the end diaphragm tend to move together during the thawing operation, to thereby change the predetermined location of those two diaphragms. A precise and predetermined positioning of the end and intermediate diaphragms relative to each other and relative to the needle is important for proper piercing and mixing operations.

A wire clip surrounds the vial and has ends which are pointed and which drag along the sidewall of the cup-shaped plastic holder during the mixing operation. Reverse movement of the vial out of the holder is prevented since the ends of the clip would tend to dig into the holder. Thus after the mixing operation, the vial is held in a fixed position relative to the holder so that air may be expressed from the vial and so that the plunger may be retracted to aspirate blood prior to injection of the medicament.

The opening in the sidewall of the needle is dimensioned so that it bridges the pierced portion of the intermediate diaphragm after the mixing operation. This ensures the complete evacuation of diluent from its chamber and ensures that air will not be trapped between the end of the needle and the intermediate diaphragm when air is expressed from the first chamber prior to injection.

The pointed needle within the holder is maintained sterile by a rubber sleeve. The sleeve also ensures that the window opening in the needle will be maintained closed until that opening emerges from the end diaphragm as that diaphragm is pierced.

According to another aspect of this invention, the syringe comprises two glass cylinders. The glass cylinders are axially butted against an intermediate diaphragm or each cylinder may be provided with its own diaphragm and then butted against the other. An end diaphragm and a plunger close the non-butted ends of the cylinders, and the cylinder closed by the plunger is provided with a powder while the cylinder closed by the end diaphragm is filled with a diluent. A transparent plastic tube telescopingly embraces the cylinders and the entire assembly is received within a cup-shaped injection holder similar to the previously described holder, and a mixing operation is accomplished by providing axial pressure on the vial to sequentially pierce the two diaphragms.

The principles of this invention may be employed to provide a medicament feed cartridge for dispensing metered amounts of mixed medicaments into the medicament pressurizing chamber of a needleless, hypojet injector. For such use, a vial may be provided with a stopper rather than a plunger closing the end of the chamber containing the powdered medicament and the hypojet injector is provided with a cup-shaped holder. A diaphragm piercing needle in the cup-shaped holder communicates with the injector pressurizing chamber so that the mixed medicaments may be fed to the pressurizing chamber.

According to a further aspect of this invention, two, necked glass tubes are provided. The necked ends of the glass tubes are butted against an intermediate diaphragm or are each provided with their own diaphragm or stopper. The necks are banded together and a diluent is provided in one tube while a powdered medicament is provided in the other tube. The end of the diluent containing tube is provided with an end diaphragm and the end of the other tube is provided with a plunger. The assembly is mounted in a holder of the type previously described.

BRIEF DESCRIPTION OF THE DRAWINGS

FIG. 1 is a cross sectional view of a syringe according to one aspect of this invention;

FIG. 1a is a fragmentary perspective view of a wire clip illustrating its position relative to the cup-shaped holder;

FIG. 2 is a cross sectional view similar to FIG. 1, but showing component parts of the syringe in positions attained after initiating a mixing operation;

FIG. 3 is a cross sectional view similar to FIGS. 1 and 2, but showing component parts of the syringe in positions attained after completion of the mixing operation and prior to an injection operation;

FIG. 4 is a fragmentary, cross sectional view illustrating an alternate arrangement for locking the intermediate diaphragm relative to the vial;

FIG. 8 is a fragmentary, cross sectional view of a syringe similar to the syringe illustrated in FIGS. 1 to 3, but showing a modification to the holder;

FIG. 9 is a fragmentary, cross sectional view of a syringe similar to FIG. 8 but showing component parts to the syringe in positions attained after initiating a mixing operation;

FIG. 10 is a fragmentary, cross sectional view of a syringe similar to FIGS. 8 and 9 but showing component parts of the syringe in positions attained after completion of the mixing operation and prior to an injection;

FIGS. 13 through 17 are cross sectional views illustrating the sequential steps employed to fill and assemble the syringe illustrated in FIGS. 1 through 3, but showing a modified plunger arrangement;

FIG. 18 is a cross sectional view of a mixing vial suitable for use with a hypojet injector;

FIG. 19 is a cross sectional view similar to FIG. 18, but showing component parts of the vial in positions attained after initiating a mixing operation; and FIG. 20 is a cross sectional view similar to FIGS. 18 and 19, but showing component parts of the vial in positions attained after completion of the mixing operation and prior to a dispensing operation.

DETAILED DESCRIPTION OF THE INVENTION

Figure 5:
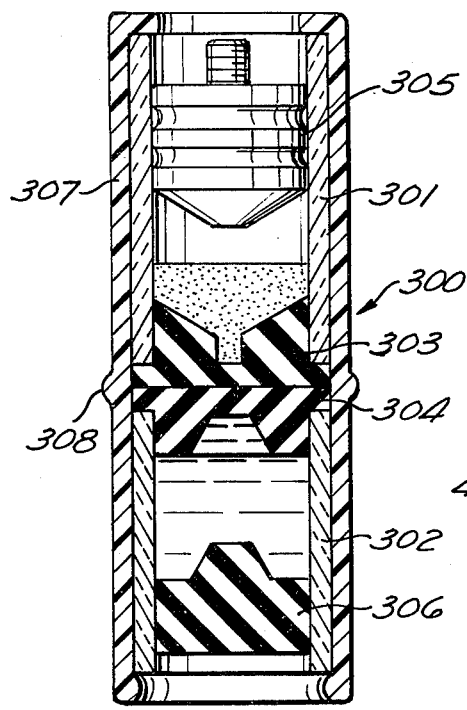
FIG. 5 is a cross sectional view of a syringe according to a further aspect of this invention.

Referring now to FIGS. 1 through 3 of the drawings, a two-chamber syringe 10 for mixing a powder medicament with a diluent and then dispensing the mixed ingredients is disclosed. The syringe 10 includes a vial means comprising a glass cylinder 11 having a plunger 12 closing one end thereof. The other end of the cylinder 11 is closed by an end diaphragm 13 and has a radially inwardly extending bead 28. The end diaphragm 13 is provided with a plurality of circumferential ribs 14 which form a fluid-type sliding seal between the end diaphragm 13 and the cylinder 11. Similarly, the plunger 12 is provided with a plurality of circumferential ribs 15 to provide a seal between the plunger 12 and the cylinder 11. An intermediate diaphragm 16 is positioned between the plunger 12 and the end diaphragm 13 to divide the interior of the cylinder 11 into first and second chambers 17 and 18, respectively. The first chamber 17 is partially filled with a powdered medicament 19 and the second chamber 18 is filled with a diluent 20, such as water.

The intermediate diaphragm 16 and the cylinder 11 have coacting parts that lock the intermediate diaphragm against axial movement toward the plunger 12 and against axial movement toward the end diaphragm 13. These coacting parts include an inwardly necked portion of the cylinder 11, which provides an inwardly extending circumferential rib 21 in the sidewall of the cylinder 11 and a circumferential groove 22 in the exterior sidewall of the cylinder 11. The rib 21 cooperates with a circumferential recess 23 in the intermediate diaphragm 16 to securely lock the diaphragm 16 in its illustrated position.

For premixing the powder and diluent and for preforming an injection, the cylinder 11 is mounted in a cup-shaped holder 25. The holder 25 is provided with a cylindrical bore 26 which receives the cylinder 11 and has a closed end or base 27. In order to prevent reverse movement of the cylinder 11 relative to the holder 25 and to permit aspiration of the device, there is provided a wire clip 29 which surrounds the necked portion of the cylinder. The wire clip has prongs 30 which are directed toward the open end of the cup-shaped holder and which tend to dig into the sidewall if one attempts to pull the cylinder 11 out of the holder 25.

The cylinder 11 is inserted into the open end of the bore until the prongs 30 snap over a rim 31. In this position, the end diaphragm 13 abuts or is slightly spaced from a pointed end 32 of a diaphragm piercing hollow needle 33, which is received within a conically recessed portion 34 of the end diaphragm 13. The needle 33 has a window opening 35 therein and is rigidly mounted coaxial with respect to a cylindrical, projecting end abutment portion 36 on the base 27. The base of the needle 33 terminates in a tapered nib 40.

In fluid communication with the interior of the needle 33, is a hollow injection needle 41 having a pointed injection end 42. To maintain the sterility of the injection needle 41 and to protect the user, a combination needle guard and plunger actuator 43 encases the needle 41 and frictionally engages the tapered nib 40 which depends from the bottom of the holder 25. For reasons which will hereinafter become apparent, the pointed end 42 of the needle 41 is embedded in a soft rubber plug 45 in the actuator 43. It will be appreciated by those skilled in the art that the needle 41 need not be intimately associated with the holder 25, but may comprise a standard detachable needle having an end fitting which frictionally engages the tapered nib 40 after removal of the actuator 43 therefrom. If such a needle is employed, means (not shown) would be provided to temporarily plug the cylindrical bore through the base of the holder during the mixing operation, which will hereinafter be explained.

In order to maintain sterility of the needle 33 prior to the mixing operation and to block the opening 35 in the needle 33 during the mixing operation, a gum rubber sleeve 50 is provided to surround the sterile needle 33 and to butt and be compressed against the end diaphragm 13.

To mix the diluent 20 with the powdered medicament 19, axial pressure is applied to a rim guard 52 at the upper end of the cylinder 11 to apply axial force to the cylinder. As this axial force is applied, the cylinder 11 moves downwardly toward the base 27. Downward movement of the cylinder 11 causes the pointed end 32 of the needle 33 to pierce the diaphragm 13 and to enter the second chamber 18, since the diaphragm 16 is locked relative to the cylinder 11 and the diaphragm 13 is hydraulically locked relative to the diaphragm 16.

Further axial movement of the cylinder 11 causes the needle 33 to pierce the intermediate diaphragm 16 and the component parts of the syringe 10 assume the position illustrated in FIG. 2. In this position, the abutment portion 36 engages the end diaphragm 13 and the opening 35 in the needle is in fluid communication with the diluent 20 in the chamber 18. If the powdered medicament 19 is pre-dried and then introduced to the chamber 17, so that the chamber 17 is under atmospheric pressure, the abutment portion 36 will force the diaphragm 13 toward the diaphragm 16 to force the diluent 20 into the chamber 17 while the volume of the chamber 18 is reduced to essentially zero. If the powdered medicament 19 is lyophilized in the chamber 17, and therefore the chamber 17 is at a sub-atmospheric pressure, the liquid will be drawn through the hollow needle 33 into the chamber 17 as soon as the hollow needle 33 communicates with the chamber 17 and the opening 35 communicates with the chamber 18. In this instance, continued axial force should be exerted on the cylinder to ensure that the end diaphragm will not be drawn toward the pointed end of the needle 33 and block the opening 35. In either case, however, it is important that the distance between the top surface of the abutment portion 36 and the needle opening 35 be such that at least a portion of the needle opening 35 be located in the chamber 18 when the abutment portion 36 engages the end diaphragm 13 and when the needle 33 pierces the intermediate diaphragm 16. Without such communication, the diluent 20 would tend to displace the intermediate diaphragm upon further movement of the cylinder downwardly. It may be noted that there is no flow toward the needle 41 since its pointed end 42 is blocked to provide an air lock below the opening 35, and it may also be noted that the sleeve 50 is pushed downwardly along the needle shank.

Further axial movement of the cylinder 11 towards the base 27 causes or permits the diluent 20 to flow into the chamber 17 and be mixed with the powdered medicament 19 as the chamber 18 collapses or is collapsed to substantially zero volume, as illustrated in FIG. 3. It may be noted that with the component parts of the syringe 10 in the positions illustrated in FIG. 3, the axial extent to the window opening bridges the pierced portion of the intermediate diaphragm 16 to ensure complete evacuation of the chamber 18.

After the chamber 18 has been fully collapsed and the powdered and liquid medicaments mixed in the chamber 17, the actuator 43 is removed and one threaded end 61 of the actuator 43 is threaded onto a stud 62 which is molded into the plunger 12. Prior to an injection, the syringe 10 may be inverted and any air trapped in the chamber 17 may be expressed from the needle 41 by placing the index and middle fingers on holder flanges 63 and 64 and advancing the plunger 12 by placing the thumb on a head portion 65 of the actuator until a few drops of medicament are expressed from the pointed end 42 of the needle. This operation is facilitated by providing a conical recess 66 in the intermediate plunger 16 to ensure that air will be trapped in the area of the opening 35 ahead of the rising column of medicament.

An injection may then be performed by inserting the pointed end 42 of the needle into the skin of the patient. If desired, the syringe 10 may be aspirated by retracting the plunger slightly and noting whether or not blood is drawn into the chamber 17. For this reason, it is desirable that the holder 25 be made from a transparent or translucent plastic material so that aspiration may be observed. The chamber 17 is substantially completely evacuated by movement of the plunger 12 into contact with the intermediate diaphragm 16 since the plunger 12 has a conical surface 67 which mates with the conical recess 66 in the intermediate diaphragm 16. Furthermore, an axial recess 68 is provided in the plunger 12 to receive the pointed end of the piercing needle 33.

Other arrangements may be provided to lock the intermediate diaphragm against movement at least toward the plunger 12. For example, in FIG. 4 there is illustrated an intermediate diaphragm 70 which is locked relative to a cylinder 71 by a radially projecting rib 72 on the diaphragm 70 which cooperates with a radial bulge 73 in the sidewall of the cylinder 71.

Referring now to FIG. 5, there is illustrated a two-chamber vial 300 according to a further aspect of the invention. The vial 300 includes two cut glass tubes 301 and 302. The use of cut tubing greatly minimizes the cost of the unit since such tubing is less expensive than tubing having beaded end portions. An intermediate diaphragm means comprises a flanged rubber stopper 303 closing one end of the tube 301 and a flanged stopper 304 closing one end of the tube 302. The tubes 301 and 302 may be respectively filled with a powdered medicament and a diluent at separate locations and respectively provided with a plunger 305 and an end diaphragm 306. In order to form the vial 300, the two previously described sub-assemblies are telescoped into a plastic jacket 307 by sliding them through a beaded open end portion 308 of the jacket. The vial 300 may then be inserted into a cup-shaped holder such as the holder 25 shown in FIGS. 1 through 3 and operated in the previously described manner. It will be noted that the jacket 307 is provided with a circumferential bead 308 which is adapted to form an interference fit with the cut-shaped holder to permit the syringe to be aspirated.

Figure 6:
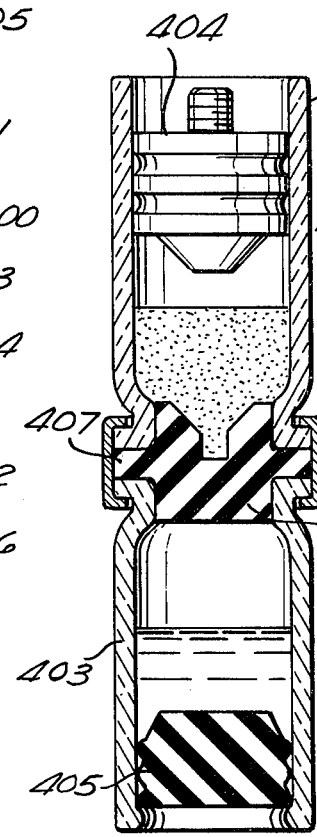
FIG. 6 is a cross sectional view of a syringe according to a further aspect of this invention.
Figure 7:
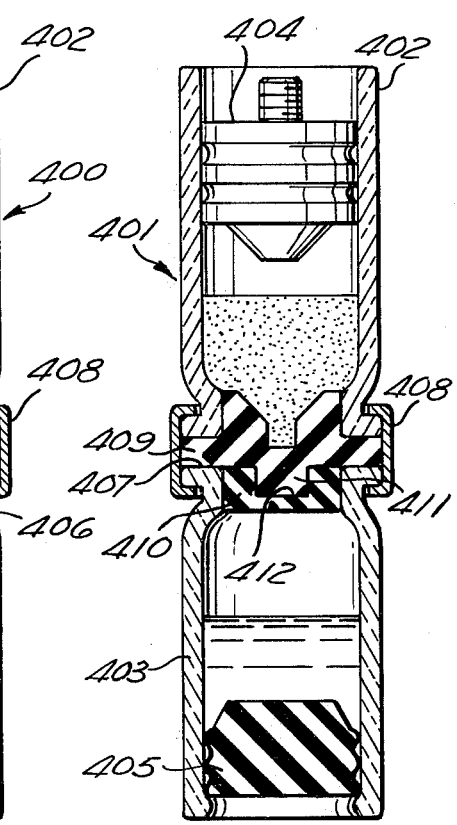
FIG. 7 is a cross sectional view similar to FIG. 6, but showing a modification of the intermediate diaphragm.

In FIGS. 6 and 7 there are illustrated vials 400 and 401 according to still further aspects of the invention. The vials 400 and 401 comprise open ended, but otherwise standard, medicament bottles or vials 402 and 403 respectively closed at one end by a plunger 404 and by an end diaphragm 405. In the embodiment illustrated in FIG. 6 an intermediate diaphragm means comprises a single piece of rubber 406 which enters the necks of the vials 402 and 403 and which is mechanically locked from axial movement relative to the vials by an annular flange 407 interposed between the vials 402 and 403. The vials are clamped together by an annular band 408 which is crimped over the neck flanges and the vial 402 is filled with a powdered medicament while the vial 403 is filled with a diluent. By providing the vial 400 with a wire clip, such as the wire clip 29, and inserting the vial in a cup-shaped holder, the contents of the vial may be mixed and dispensed in the previously described manner. This arrangement is particularly suited for dispensing relatively large doses wherein a vial having the cylindrical configuration shown in FIGS. 1 through 3 would be excessively long or have an excessive diameter. If the vial is excessively long the needle 33 of the cup-shaped holder would project excessively into the chamber containing the mixed ingredients, thus necessitating the use of a longer plunger to accommodate the projecting needle. If on the other hand, the vial is made with an excessive diameter, the plunger and intermediate diaphragms would have more bulk and present an excessive rubber area to the medicament to thereby cause possible instability to the medicament. Since in FIG. 6 the intermediate diaphragm is located in a relatively narrow neck portion of the vial, a smaller area of rubber is exposed to the medicament.

The arrangement shown in FIG. 7 is similar to the embodiment of FIG. 6 and therefore possesses all its advantages. However, the intermediate diaphragm comprises a first diaphragm 409 and a second diaphragm 410 which are respectively received within the neck portions of the vials 402 and 403. The diaphragm 409 is provided with a projection 411 which is received within a recess 412 in the diaphragm 410. This arrangement permits the diluent and powder filling operations to be conducted at different locations.

In the embodiment illustrated in FIGS. 8 through 10 there is illustrated another approach to the problem of needle projection when using a relatively large dosage syringe. The syringe 500 illustrated in those Figures has component parts which are similar to the component parts illustrated in the embodiment of FIGS. 1 through 3 and those similar parts are provided the same reference numerals. A compression spring 501 is positioned within an abutment means 502 to surround a diaphragm piercing needle 503. It may be noted that the needle 503 does not have a window opening but has a bevel which will span the thickness of the pierceable portion of the intermediate diaphragm.

The syringe 500 may be activated by applying axial pressure to the rim guard 52 at the upper end of the cylinder 11 to apply axial force to the cylinder. As this axial force is applied the cylinder moves downwardly toward the base 27 and the force causes the pointed end 504 of the needle 503 to pierce the diaphragm 13 and to enter the second chamber 18 while the spring 501 is compressed between the diaphragm 13 and the base 27.

Further axial movement of the cylinder causes further compression of the spring 501 and causes the needle 503 to pierce the intermediate diaphragm (FIG. 9). As soon as the end of the needle enters the first chamber 17 and with a relatively long beveled portion providing fluid communication between the chambers 17 and 18, the hydraulic lock in the chamber 18 is relieved and the stored energy in the spring drives the end diaphragm 13 toward the diaphragm 16 to force the diluent into the chamber 17 while the volume of the chamber 18 is reduced essentially to zero. The position of the spring 501 in FIG. 3 is considered herein to be an abutment. It may be noted therefore that the point of the needle need not project into the chamber 17 to the extent necessary in the embodiment of FIGS. 1 through 3, i.e. the axial extent of the chamber 18.

Figure 11:
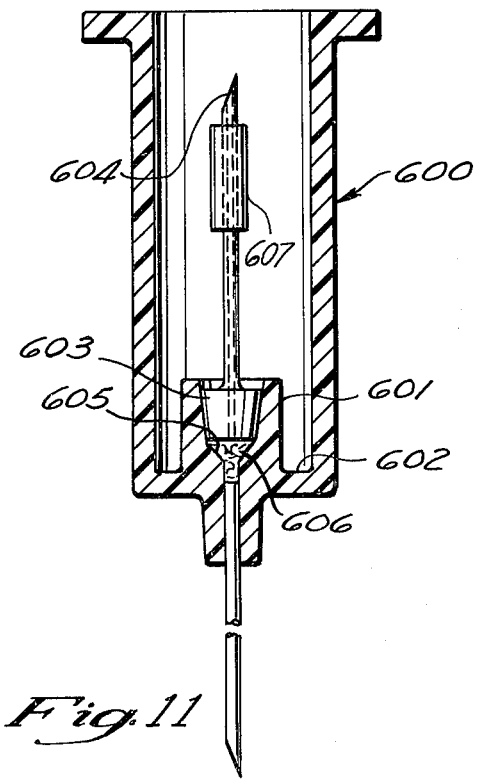
FIG. 11 is a fragmentary, cross sectional view of a modified holder.

Turning now to FIG. 11, a modified cup-shaped holder 600 is illustrated. The holder 600 includes a tapered receptable 601 in its base 602 which receives a tapered nib portion 603 of a diaphragm piercing needle 604. The needle 604 may be made from a hard plastic and has a window opening (not shown) covered by a rubber sleeve 607. A conical chamber 605 is formed at the bottom of the receptacle 601 and this chamber is provided with a suitable filter 606 such as wire gauze, open celled foam or the like.

Figure 12:
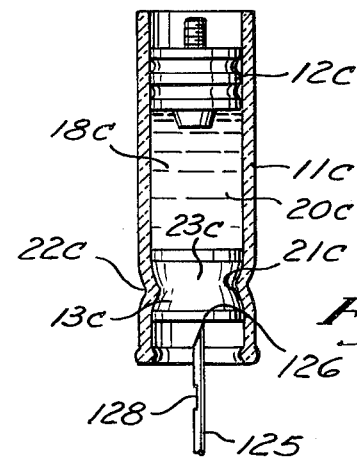
FIG. 12 is a cross sectional view of a one-chamber injection syringe showing a diaphragm locking arrangement according to this invention.

Referring now to FIG. 12, there is illustrated a single chamber device or "wet unit" which employs the diaphragm locking means according to this invention. The single chamber device comprises a cylinder 11c closed at one end by a slidable plunger 12c and at the other end by an end diaphragm 13c. The cylinder 11c, the end diaphragm 13c, and the plunger 12c define a chamber 18c containing a liquid medicament 20c. The end diaphragm 13c and the cylinder 11c having coacting parts that lock the diaphragm 13c against axial movement toward the plunger 12c and against axial movement out of the cylinder 11c. These coacting parts include an inwardly necked portion of the cylinder 11c, which provides an inwardly extending, circumferential rib 21c in the sidewall of the cylinder 11c and a circumferential groove 22c in the exterior sidewall of the cylinder 11c. The rib 21c cooperates with a circumferential recess 23c in the diaphragm 13c to securely lock the diaphragm 13c in its illustrated position. An injection may be performed by inserting the cylinder 11c in a cup-shaped holder and applying axial force to the cylinder 11c so that the pointed end 126 of the needle 125 pierces the end diaphragm 13c and then applying axial force to the plunger 12c to express medicament through the injection needle. Although the window opening 128 in the needle 125 is not absolutely essential for injecting the medicament 20c, it is desirable to provide such an opening so that air may be properly expressed from the unit prior to an injection. Therefore, the window opening should be spaced above the base of the cup-shaped holder a distance which slightly exceeds the thickness of the pierceable portion of the diaphragm 13c.

Referring now to FIGS. 13 through 17, there is illustrated a technique for filling the cylinder 11 with a liquid diluent and a powdered medicament, and for assembling the diaphragms and plunger therein. The assembly technique includes the initial step of inserting the end diaphragm 13 into the non-beaded end (or upper end of the cylinder as viewed in FIG. 13) by a suitable cylindrical tool until the end diaphragm attains the position illustrated in FIG. 13 slightly above the projection 21. A metered amount of the diluent 20 is then introduced into the cylinder and the intermediate diaphragm 16 is pushed into the cylinder until it contacts the upper surface of the diluent 20. To permit air to escape during the insertion of the intermediate diaphragm 16, a wire 150 is positioned against the inner sidewall of the cylinder 11 to provide a path for the trapped air. After the intermediate diaphragm 16 contacts the liquid 20, the wire 150 is removed and a cylindrical tool 151 having a conical end portion 152 is brought into engagement with the intermediate diaphragm 16 to force it, and therefore the liquid 20 and the end diaphragm 13, downwardly as indicated in FIG. 14. The assembly of the two diaphragms and the liquid 20 is complete when the recess 23 of the intermediate diaphragm engages the projection 21 as is indicated in FIG. 15.

If the diluent 20 has not been added aseptically, it is necessary to autoclave the assembly shown in FIG. 15 prior to adding the powdered medicament. If any air is trapped in the diluent chamber, a pressure of about 15 psi will build up in the diluent chamber during autoclaving at 250°F. The bead 28 serves to retain the end diaphragm 13 in the cylinder 11 as the end diaphragm is moved toward the end of the cylinder under the pressure of the expanding gas and liquid.

After autoclaving, a measured amount of powdered medicament is placed in the open end of the cylinder 11 and that end is closed by the plunger 12 and the rim guard 52 (FIGS. 1 - 3).

The powdered medicament may be lyophilized or freeze-dried, however, in the unit, as is shown in FIGS. 16 and 17. In FIG. 16, a measured amount of medicament 155, adapted to be freeze-dried or lyophilized, is metered into the upper open end of the cylinder 11 and a rubber plunger 156 is partially inserted in the cylinder 11. The rubber plunger 156 comprises a cylindrical plug having a first cylindrical portion 157 and a second cylindrical portion 158. The first cylindrical portion 157 includes a pair of beads 159, which are separated by a land 160 and which have a diameter which is slightly greater than the inside diameter of the cylinder 11, to thereby effect a substantially liquid-tight seal with the cylinder when the beads are positioned as indicated in FIG. 17. The second cylindrical portion 158 includes a plurality of axially extending and radially projecting ribs 161 which are defined by axially extending slots 162. The slots 162 and the ribs 161 define axial passageways to the interior of the cylinder 11 when the plunger is partially inserted in the cylinder 11, as illustrated in FIG. 16.

With the component parts assembled as illustrated in FIG. 16, the assembly is placed in a lyophilization chamber and is subjected to a conventional freeze-drying cycle to remove substantially all of the moisture from the chamber 17. As is more fully set forth in the copending application of Hurschman, Ser. No. 256,407, filed May 24, 1972 now U.S. Pat. No. 3,810,469, the assembly is subjected to extremely low temperatures to freeze the medicament in the chamber 17. The freezing process is controlled in a known manner so that the ice formation has a multiplicity of cracks or spaces between ice crystals. After the medicament is frozen, the frozen liquid matrix is removed by evacuating the lyophilization chamber to thereby subject the frozen medicament to extremely low pressures. In some instances, an inert gas at low pressures is admitted to the chamber. The frozen liquid matrix is thereby drawn off or sublimed as a vapor through the passageways provided by the ribs 161 and the slots 162 and the plunger 156. When the moisture has been removed from the chamber 17, and while the vacuum is applied, the plunger 156 is driven to the position illustrated in FIG. 17 to seal the chamber 17 containing the now-powdered medicament 19 therein.

During the freeze-drying operation, the liquid diluent 20 in the chamber 18 freezes and expands to drive the end diaphragm 13 to the position indicated in phantom outline in FIG. 16. Since the intermediate diaphragm 16 is locked in position, no movement of that diaphragm is possible. Therefore, upon melting of the diluent 20, the end diaphragm 13 merely returns to its predetermined position in the cylinder 11.

Referring now to FIGS. 18 through 20 of the drawings, a two-chamber vial 200 for mixing a powder medicament with a diluent and then dispensing the mixed ingredients is disclosed. The vial 200 is particularly useful where the powder and liquid medicaments are to be mixed in the vial and then conveyed to or through an intervening instrumentality for subsequent injection into the patient rather than injection by a needle directly associated with the vial 200. For example, the diaphragm piercing needle may communicate with tubing which in turn communicates with an I.V. tube by a standard Y connection so that antibiotics may be periodically added to the flowing I.V. solution for injection into the patient's vein. A further use for the vial 200 is illustrated in FIGS. 18 through 20 of the drawings, which illustrate an assembly for dispensing mixed medicaments into the medicament pressure chamber of a needleless hypojet injector.

The vial 200 includes a glass cylinder 201 having one end thereof provided with a standard bottle neck 202 closed by a standard lyophilization stopper 203. The other end of the cylinder 201 is closed by an end diaphragm 204, which forms a fluid-tight sliding seal within the cylinder 201. An intermediate diaphragm 205 is positioned between the stopper 203 and the end diaphragm 204 to divide the interior of the cylinder 201 into first and second chambers 206 and 207, respectively. The first chamber 206 is partially filled with a powdered medicament 208 and the second chamber 207 is filled with a diluent 209, such as water.

The intermediate diaphragm 205 and the cylinder 201 having coacting parts that lock the intermediate diaphragm against axial movement toward the stopper 203 and against axial movement toward the end diaphragm 204. These coacting parts include an inwardly necked portion of the cylinder 201, which provides an inwardly extending, circumferential rib 210 in the sidewall of the cylinder 201 and a circumferential groove 211 in the exterior sidewall of the cylinder 201. The rib 210 cooperates with a circumferential recess 212 in the intermediate diaphragm 205 to securely lock the diaphragm 205 in its illustrated position.

For premixing the powder and diluent, and for providing a passageway to a medicament pressurizing chamber (not shown) of a needleless hypojet injector, the cylinder 201 is mounted in a cup-shaped holder 213 which projects from a portion 214 of a needleless hypojet injector. The holder 213 is provided with a cylindrical bore 215 which receives the cylinder 201 and has its end closed by the portion 214. The end of the cylinder 201 is provided with radially inwardly and outwardly extending beads 216 and 217, respectively, and the bead 217 is initially retained between upper and lower rows of projections 218 and 219, respectively, which are arranged in spaced, circumferential arrays about the inner sidewall of the bore 215. The cylinder 201 is inserted into the open end of the bore until the bead 217 snaps over the projections 218 and is stopped by the projections 219. In this position, the end diaphragm 204 abuts or is slightly spaced from a pointed end 220 of a diaphragm piercing hollow needle 221, which is received within a conically recessed portion 222 of the end diaphragm 204. The needle 221 has a window opening 223 therein and is rigidly mounted within a cylindrical, projecting end abutment portion 224 on the portion 214. The interior of the needle 221 communicates with the medicament pressurizing chamber (not shown) of the hypojet injector.

In order to maintain sterility of the needle 221 prior to the mixing operation and to block the opening 223 in the needle 221 during the mixing operation, a gum rubber sleeve 225 is provided to surround the sterile needle 221 and to butt and be compressed against the end diaphragm 204. To further maintain sterility, or as an alternative to the sleeve 225, an O-ring 226 may be provided in the circumferential groove 211 and in sealing engagement with the bore 215. The O-ring 226 serves to trap a sterile gas in the space surrounding the needle 221.

To mix the diluent 209 with the powdered medicament 208, axial pressure is applied to the upper end of the cylinder 201. As this axial force is applied, the bead 217 will snap past the projections 219 so that the cylinder moves downwardly toward the portion 214. To prevent entrapment of the sterile gas, axially extending slots or grooves 227 are cut into the inner sidewall of the bore 215 just below the initial position of the O-ring 226 and for an axial extent substantially corresponding to the travel of the O-ring along the wall. Downward movement of the cylinder 201 causes the pointed end 220 of the needle 221 to pierce the diaphragm 204 and to enter the second chamber 207, since the diaphragm 205 is locked relative to the cylinder 201 and the diaphragm 204 is hydraulically locked relative to the diaphragm 205. As the needle pierces the diaphragm 204, the sleeve 225 collapses in an accordion fashion.

Further axial movement of the cylinder 201 causes the needle 221 to pierce the intermediate diaphragm 205 and the component parts of the vial 200 assume the position illustrated in FIG. 19. In this position, the abutment portion 224 engages the end diaphragm 204 and the opening 223 in the needle is in fluid communication with the diluent 207 in the chamber 209. If the powdered medicament 208 is under atmospheric pressure, the abutment portion 224 will force the diaphragm 204 toward the diaphragm 205 to force the diluent 207 into the chamber 206 while the volume of the chamber 207 is reduced to essentially zero. If the powdered medicament 208 is lyophilized in the chamber 206, and therefore the chamber 206 is at a subatmospheric pressure, the liquid will be drawn through the hollow needle 221 into the chamber 206 as soon as the hollow needle 221 communicates with the chamber 206 and the opening 223 communicates with the chamber 207. In this instance, continued axial force should be exerted on the cylinder to ensure that the end diaphragm will not be drawn toward the pointed end of the needle 221 and block the opening 223. In either case, however, it is important that the distance between the top surface of the abutment portion 224 and the needle opening 223 be such that at least a portion of the needle opening 223 be located in the chamber 207 when the abutment portion engages the end diaphragm 204 and when the needle 221 pierces the intermediate diaphragm 205. Without such communication, the diluent 207 would tend to displace the intermediate diaphragm upon further movement of the cylinder downwardly. Means (not shown) are provided within the hypojet injector to ensure that there is no flow below the opening 223 during the diaphragm piercing operation, and it may be noted that the sleeve 225 is collapsed between the abutment portion 224 and the end diaphragm 204 in the conical recess 222.

Further axial movement of the cylinder 201 towards the portion 214 causes or permits the diluent 209 to flow into the chamber 206 and be mixed with the powdered medicament 208 as the chamber 207 collapses or is collapsed to substantially zero volume, as illustrated in FIG. 20. In this position, the bead 217 is locked at the bottom of the bore 215 by a plurality of projections 230 which extend radially inwardly from the inner surface of the bore 215. The projections 230 are relatively small to permit the vial 200 to be removed after use, and they serve primarily as a means to ensure that the vial is properly driven home in the holder. It may be noted that with the component parts of the vial 200 in the positions illustrated in FIG. 20, the axial entent of the window opening bridges the pierced portion of the intermediate diaphragm 205 to ensure complete evacuation of the chamber 207.

If the powdered medicament is provided in the chamber 206 at substantially atmospheric pressure, the chamber 206 will be slightly pressurized when the medicaments are mixed, and this pressure will aid the flow of the mixed medicaments through the needle 221 and into the medicament pressurizing chamber of the hypojet injector. However, even if the powdered medicament is lyophilized in the chamber 206 and that chamber is at subatmospheric pressure after mixing the powder with the diluent, the mixed medicaments will be drawn into the medicament pressurizing chamber upon retraction of the force applying piston (not shown) which is slidable within the pressurizing chamber.

The invention is not restricted to the slavish imitation of each and every detail set forth above. Obviously, devices may be provided which change, eliminate or add certain specific details without departing from the scope of the invention.

What is claimed is:

1. A two-chamber mixing syringe comprising:
   a. vial means;
   b. a plunger slidable within and closing one end of the vial means;
   c. an end diaphragm closing the other end of the vial means;
   d. a stationary intermediate diaphragm within said vial means separating the interior of the vial means into first and second chambers respectively defined by said plunger and intermediate diaphragm and by said intermediate diaphragm and said end diaphragm; said vial means and intermediate diaphragm having coacting parts that comprise means for locking the intermediate diaphragm against axial movement towards said plunger during a mixing operation and during a dispensing operation; said coacting parts comprising radially extending interengaging and interfering surfaces on said vial means and said intermediate diaphragm;
   e. a cup-shaped holder having a cylindrical bore closed at one end and receiving said other end of said vial means with said other end of said vial means spaced from said closed end of said bore; and
   f. hollow needle means having a pointed end within the space between said other end of said vial means and said closed end of said bore, whereby an ingredient in said first chamber may be mixed with an ingredient in said second chamber by applying axial pressure to said vial means so that said needle sequentially pierces said end diaphragm and said intermediate diaphragm and whereby said ingredients may be dispersed by advancing said plunger toward said intermediate diaphragm.

2. A two-chamber mixing syringe according to claim 1 wherein said coacting parts lock the intermediate diaphragm against movement in both directions.

3. A two-chamber mixing syringe according to claim 2 wherein said needle means includes another pointed end projecting from said holder in axial alignment with the pointed end within said space and in fluid communication therewith.

4. A two-chamber mixing syringe according to claim 2 wherein said needle means has an opening therein spaced from said pointed end.

5. A two-chamber mixing syringe according to claim 4 wherein said intermediate diaphragm and said end diaphragm have axially aligned pierceable portions.

6. A two-chamber mixing syringe according to claim 5 wherein the axial longitudinal extent of said needle opening exceeds the thickness of the pierceable portion of said intermediate diaphragm.

7. A two-chamber mixing syringe according to claim 6 wherein the needle means within said space projects from end abutment means extending from the closed end of said bore.

8. A two-chamber mixing syringe according to claim 7 wherein the abutment means is adapted to be received within said other end of said vial means.

9. A two-chamber mixing syringe according to claim 7 wherein the distance between the abutment means and the opening in the needle does not substantially exceed the thickness of said end diaphragm.

10. A two-chamber mixing syringe according to claim 7 wherein the distance between said abutment means and the pointed end of the needle exceeds the combined axial extents of the thickness of said end diaphragm, the second chamber and the pierceable portion of said intermediate diaphragm.

11. A two-chamber mixing syringe according to claim 2 wherein portions of the intermediate and end diaphragms defining said second chamber are complementary surfaces for mating engagement.

12. A two-chamber mixing syringe according to claim 2 wherein portions of said plunger and said intermediate diaphragm defining said first chamber are complementary surfaces for mating engagement.

13. A two-chamber mixing syringe according to claim 4 wherein said opening is covered by a flexible sleeve which surrounds said needle.

14. A two-chamber mixing syringe according to claim 2 wherein said coacting parts include an inwardly extending circumferential rib in the vial means which cooperate with a circumferential recess in said intermediate diaphragm.

15. A two-chamber mixing syringe according to claim 14 wherein a circumferential groove in the exterior sidewall of the vial means provides said inwardly extending circumferential rib and wherein a wire clip having prongs directed toward said one end encircles said groove.

16. A two-chamber mixing syringe according to claim 2 wherein energy storing means is provided between said end diaphragm and the closed end of said bore and is adapted to apply increasing amounts of pressure to said end diaphragm as said axial pressure is applied, whereby said energy storing means drives said end diaphragm toward said intermediate diaphragm when said needle pierces said intermediate diaphragm.

17. A two-chamber mixing syringe according to claim 16 wherein said energy storing means comprises a spring.

18. A two-chamber mixing syringe according to claim 16 wherein said needle has a beveled edge, the axial entent of which exceeds the axial extent of a pierceable portion of said intermediate diaphragm.

19. A two-chamber mixing syringe according to claim 3 wherein filter means is provided between the pointed ends of said needle means.

20. A two-chamber mixing syringe according to claim 1 wherein there is provided means between said vial and said cup-shaped holder to prevent withdrawal of said vial from said holder prior to and during axial movement of said vial and cup-shaped holder relative to each other.

21. A two-chamber mixing syringe according to claim 20 wherein said means for preventing said axial movement is located in a circumferential groove in the exterior sidewall of the vial means.

22. A two-chamber mixing syringe according to claim 9 wherein the needle has a beveled edge which constitutes said window opening.

23. A two-chamber mixing syringe comprising:
a. a glass cylinder;
b. a plunger slidable within and closing one end of the cylinder;
c. an end diaphragm closing the other end of the cylinder;
d. a stationary intermediate diaphragm within said cylinder separating the interior of the cylinder into first and second chambers respectively defined by said plunger and intermediate diaphragm and by said intermediate diaphragm and end diaphragm; said cylinder and intermediate diaphragm having coacting parts that comprise means for locking the intermediate diaphragm against axial movement toward said plunger during a mixing and during a dispensing operation; said coacting parts comprising radially extending interengaging and interfering surfaces on said vial means and said intermediate diaphragm;
e. a cup-shaped holder having a cylindrical bore closed at one end and receiving said other end of said cylinder with said other end of said cylinder spaced from said closed end of said bore; and
f. a hollow pointed needle within the space between said other end of said cylinder and said closed end of said bore, whereby an ingredient in said first chamber may be mixed with an ingredient in said second chamber by applying axial pressure to said vial means so that said needle sequentially pierces said end diaphragm and said intermediate diaphragm and whereby said ingredients may be dispersed by advancing said plunger toward said intermediate diaphragm.

24. A two-chamber mixing syringe according to claim 23 wherein said coacting parts lock said intermediate diaphragm against axial movement toward said plunger and intermediate diaphragm.

25. A two-chamber mixing syringe according to claim 24 wherein said coacting parts comprise an inwardly extending circumferential rib in the cylinder which cooperates with a circumferential recess in said intermediate diaphragm.

* * * * *

UNITED STATES PATENT AND TRADEMARK OFFICE
CERTIFICATE OF CORRECTION

PATENT NO. : 3,946,732
DATED : March 30, 1976
INVENTOR(S) : Alfred A. Hurschman

It is certified that error appears in the above-identified patent and that said Letters Patent are hereby corrected as shown below:

Front page, change the inventor's surname from "Hurscham" to -- Hurschman -- (both occurrences); and in the Abstract, line 17, after "end" insert -- and --.

Column 4, line 64, change "to" to read -- of --.

Column 7, line 19, change "to" to read -- of --.

Column 13, line 39, change "entent" to read -- extent --.

Column 14, line 27, change "dispersed" to read -- dispensed --.

Column 15, line 33, change "entent" to read -- extent --.

Column 16, line 35, change "dispersed" to read -- dispensed --.

Signed and Sealed this eighth Day of June 1976

[SEAL]

Attest:

RUTH C. MASON
Attesting Officer

C. MARSHALL DANN
Commissioner of Patents and Trademarks